(12) United States Patent
Nakatani

(10) Patent No.: US 8,729,333 B2
(45) Date of Patent: May 20, 2014

(54) ABSORPTIVE ARTICLE

(75) Inventor: Yuiko Nakatani, Sakura (JP)

(73) Assignee: Daio Paper Corporation, Ehime (JP)

( * ) Notice: Subject to any disclaimer, the term of this patent is extended or adjusted under 35 U.S.C. 154(b) by 209 days.

(21) Appl. No.: 13/498,021

(22) PCT Filed: Sep. 16, 2010

(86) PCT No.: PCT/JP2010/066059
§ 371 (c)(1),
(2), (4) Date: Mar. 23, 2012

(87) PCT Pub. No.: WO2011/037067
PCT Pub. Date: Mar. 31, 2011

(65) Prior Publication Data
US 2012/0197226 A1    Aug. 2, 2012

(30) Foreign Application Priority Data

Sep. 24, 2009   (JP) ................................ 2009-218997

(51) Int. Cl.
*A61F 13/15* (2006.01)
(52) U.S. Cl.
USPC ........... 604/375; 604/374; 604/367; 604/377; 604/378; 604/385.101
(58) Field of Classification Search
USPC ........... 604/375, 374, 367, 377, 378, 385.101
See application file for complete search history.

(56) References Cited

U.S. PATENT DOCUMENTS

| 7,265,258 B2 * | 9/2007 | Hamilton et al. ............. 604/374 |
| 2009/0157022 A1 * | 6/2009 | MacDonald et al. ......... 604/361 |

FOREIGN PATENT DOCUMENTS

| CN | 101453971 | | 6/2009 |
| EP | 1 013 290 | A1 | 6/2000 |
| JP | 64-40047 | A | 2/1989 |
| JP | 2004-187966 | A | 7/2004 |
| JP | 3648472 | B2 | 2/2005 |
| JP | 2005-67190 | A | 3/2005 |
| JP | 2007-222864 | A | 9/2007 |
| JP | 2009-50515 | A | 3/2009 |

OTHER PUBLICATIONS

Chinese Office Action dated Sep. 3, 2013 (and English translation thereof) in counterpart Chinese Application No. 201080042625.4.
International Search Report dated Nov. 2, 2010 issued in International Appln. No. PCT/JP2010/066059.
Extended European Search Report (EESR) dated Nov. 21, 2013 (in English) issued in counterpart European Application No. 10818742.8.

* cited by examiner

*Primary Examiner* — Jacqueline F. Stephens
(74) *Attorney, Agent, or Firm* — Holtz, Holtz, Goodman & Chick, PC

(57) ABSTRACT

An absorptive article 1 includes a liquid-permeable top sheet 20, a liquid impermeable back sheet 30, and an absorber 50 disposed between the top sheet 20 and the back sheet 30. The absorber 50 has a layered structure including an upper absorbent layer 511 disposed on the side of the top sheet 20 and a lower absorbent layer 512 disposed on the side of the back sheet 30. The upper absorbent layer 511 is composed of virgin pulp and virgin polymer, and the lower absorbent layer 512 contains recycled pulp and recycled polymers.

7 Claims, 10 Drawing Sheets

ABSORPTIVE ARTICLE

This application is a U.S. National Phase Application under 35 USC 371 of International Application PCT/JP2010/066059 filed Sep. 16, 2010.

TECHNICAL FIELD

The present invention relates to an absorptive article.

BACKGROUND ART

Until now, absorptive articles typified by disposable diapers and bladder control pads have been in widespread use.

These absorptive articles are usually made from pulp as a main raw material produced from wood, and most thereof are incinerated after use.

In recent years, however, various reclamation processes have been developed to recycle used products with consideration for environmental concerns such as deforestation and carbon dioxide emissions.

For example, Patent Document 1 discloses a reclaimed disposable diaper and reclaimed bladder control pad made from regenerated pulp separated and recovered from used disposable diapers and used bladder control pads.

Patent Document 2 discloses an absorptive article having an absorber that contains a blended pulp composed of virgin pulp and recycled pulp obtained from used paper, and that contains an absorbent polymer.

In processes of manufacturing the disposable diaper or the absorbent pad, rejected products occur during adjustment of a production machine at the time of an item change and material splicing. Furthermore, products that cannot be shipped due to a failure are treated as rejected products.

Although some of the rejected products have been converted to cat litter or other products after separating a polymer absorber, others have been usually incinerated.

In recent years, efforts have been made to separate pulp and polymers from rejected products and to reuse them for effective use of the rejected products.

PRIOR ART DOCUMENTS

Patent Documents

Patent Document 1: Japanese Patent No. 3648472
Patent Document 2: Publication of Japanese Unexamined Patent Application No. 64-40047

DISCLOSURE OF INVENTION

Problems to be Solved by Invention

Unfortunately, recycled pulp and polymers from rejected products are inevitably commingled with foreign materials such as rubber threads, nonwoven cloth and a polymer sheet due to performance limit of recovery equipment. Since most of these foreign materials are colored, there has been a problem in that the products made from the recycled pulp and polymers do not have a satisfactory appearance due to the commingled foreign materials.

An object of the present invention is to provide an absorptive article that has a satisfactory appearance even in the case of using recycled pulp and polymers containing foreign materials.

Means for Solving Problems

In order to solve the problems described above, according to a first aspect of the present invention, there is provided an absorptive article comprising a liquid-permeable top sheet, a liquid-impermeable back sheet, and an absorber disposed between the top sheet and the back sheet, wherein the absorber has a layered structure comprising an upper absorbent layer disposed on the top-sheet side and a lower absorbent layer disposed on the back-sheet side; the upper absorbent layer comprises virgin pulp and virgin polymer, and the lower absorbent layer contains recycled pulp and recycled polymer.

According to a second aspect of the present invention, the lower absorbent layer of the absorptive article according to the first aspect of the present invention contains virgin pulp and virgin polymer.

According to a third aspect of the present invention, the back sheet of the absorptive article according to the first aspect of the present invention has a predetermined color or pattern.

According to a fourth aspect of the present invention, the absorptive article according to the first aspect of the present invention further comprises a second back sheet that covers a surface of the back sheet, the surface being opposite to another surface of the back sheet on the top-sheet side.

According to a fifth aspect of the present invention, the absorber of the absorptive article according to the first aspect of the present invention is covered with crepe paper having a predetermined color or pattern.

According to a sixth aspect of the present invention, the absorber of the absorptive article according to the first aspect of the present invention is covered with a sheet containing activated carbon.

According to a seventh aspect of the present invention, the absorptive article according to the first aspect of the present invention further comprises a liquid-permeable second sheet that covers a surface of the top sheet, the surface being opposite to another surface of the top sheet on the back-sheet side.

Effects of Invention

An absorptive article of the present invention includes a liquid-permeable top sheet, a liquid-impermeable back sheet, and an absorber disposed between the top sheet and the back sheet. The absorber has a layered structure including an upper absorbent layer disposed on the top-sheet side and a lower absorbent layer disposed on the back-sheet side. The upper absorbent layer is formed of virgin pulp and virgin polymer, and the lower absorbent layer contains recycled pulp and recycled polymer obtained from rejected products during manufacturing processes.

Since the recycled pulp and polymers are used only in the lower absorbent layer, foreign materials commingled with the recycled pulp and polymer are inconspicuous when the absorptive article is seen from the top. Thus, the absorptive article provides a satisfactory appearance even in the case of using recycled pulp and polymers containing foreign materials.

EMBODIMENTS FOR CARRYING OUT INVENTION

Figure 1:
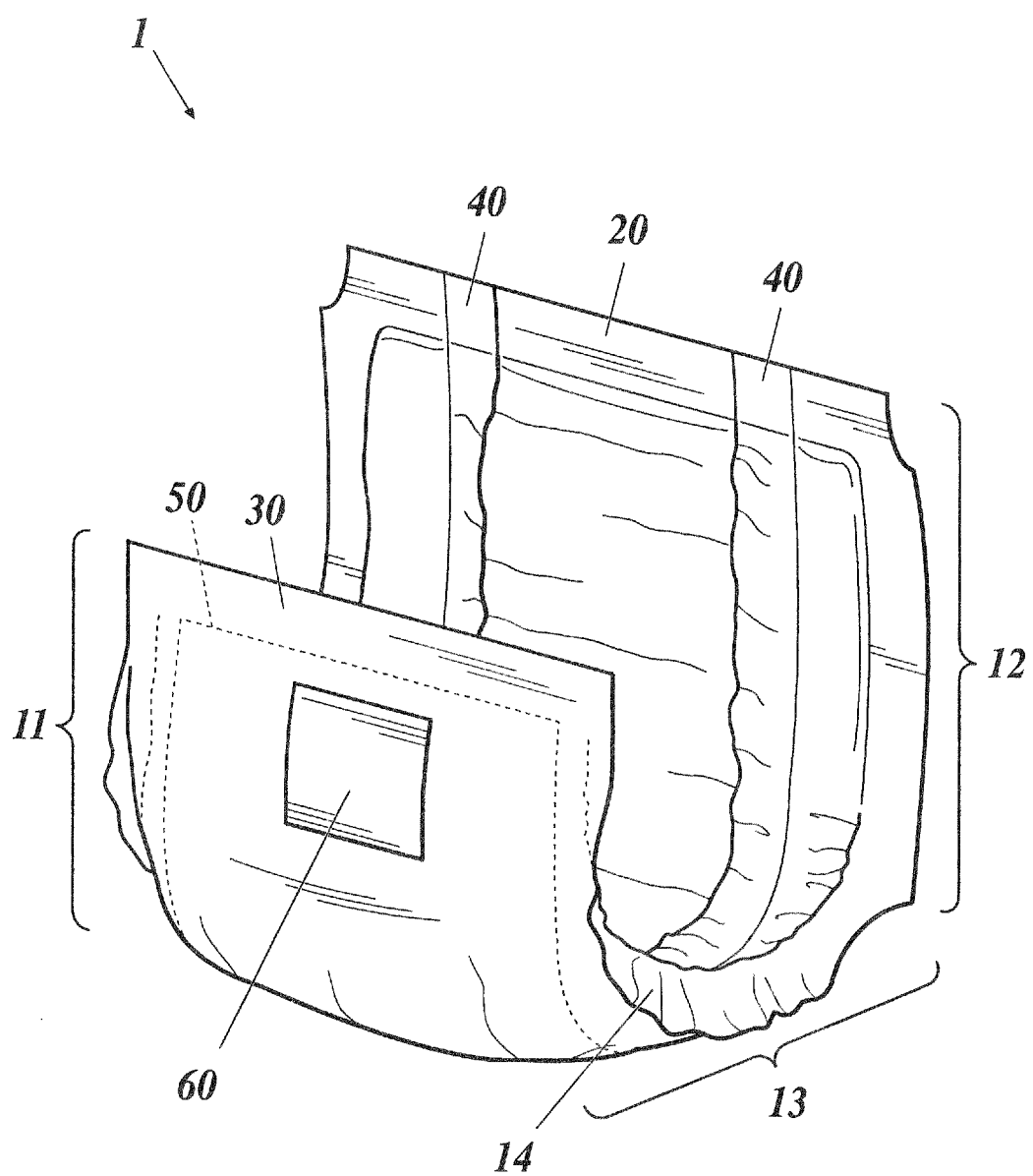
FIG. 1 is a perspective view illustrating an absorptive article of the present embodiment in a wearable state.

Embodiments of the present invention will now be described in details with reference to the attached drawings. The scope of the invention should, however, not be limited to the embodiments illustrated in the drawings.

In the following description, a portion to cover a human (wearer's) belly side when the absorptive article is worn is referred to as front side, a portion to cover a wearer's back side is referred to as back side, a portion to be in contact with the wearer is referred to as upper side, a portion opposite side of the contact surface is referred to as lower side, and a direction perpendicular to both the anteroposterior direction and the vertical direction is defined as transverse direction, in a development view of an absorptive article 1 of this embodiment.

The absorptive article 1, which functions as, for example, a bladder control pad for night use or for long-time use, is detachably and exchangeably attached to an outer body (not illustrated), such as a diaper, a diaper cover, or underpants, to be worn by a human body for use.

The absorptive article 1 is to cover a crotch portion of a wearer from a belly side to a back side when worn.

Specifically, one end portion (front end portion) of the absorptive article 1 constitutes a belly side portion 11 to cover the wearer's belly side when worn, another end portion (back end portion) constitutes a back side portion 12 to cover the wearer's back, and a portion between the belly side portion 11 and the back side portion 12 constitutes a crotch portion 13 to be located under wear's crotch.

The back side portion 12 has a length in the anteroposterior direction longer than that of the belly side portion 11, and has a length in the transverse direction longer than those of the belly side portion 11 and the crotch portion 13. Thus, a wide area in the back of the wearer can be covered with the back side portion 12.

Both edges of the crotch portion 13 constitute two leg periphery portions 14 to be located around legs of the wearer from the belly side portion 11 to the back side portion 12 when worn. The leg periphery portions 14 and 14 have respective flat-gather elastic members 141, such as rubber threads. The flat-gather elastic members 141 constitute flat gathers. This allows the absorptive article 1 to stretchably fit around the wearer's legs. Thereby, leakage at the edges is prevented, and the absorptive article 1 can easily follow the movement of the wearer's body without slippage. The flat gathers allow the absorptive article 1 to be naturally curved, so that three-dimensional gathers (to be described later) can be tightly attached to the wearer's crotch portion.

The absorptive article 1 mainly includes a liquid-permeable top sheet 20 arranged as a surface to be in contact with a wearer (upper side); a liquid-impermeable back sheet 30 arranged on the other side of the surface to be in contact with the wearer (lower side); an absorber 50 disposed between the top sheet 20 and the back sheet 30; gather sheets 40 and 40 arranged at both side edges (right edge and left edge) of the absorber 50, with respect to the width direction thereof, over the top sheet 20 along the longitudinal direction (anteroposterior direction) of the absorptive article 1; and a fixing member 60 arranged at the belly side portion 11 of the back sheet 30 for fixing the absorptive article 1 to an outer body.

The top sheet 20, which constitutes a surface to be in contact with the wearer who wears the absorptive article 1, is composed of a liquid-permeable sheet that is arranged over the absorber 50 to receive body fluid and transport it to the absorber 50.

Examples of materials suitable for the liquid-permeable sheet include plain-woven nets of nylon or polyethylene terephthalate yarn, films or sheets having a large number of through holes, polyethylene or polypropylene films or sheets, and liquid-permeable woven or non-woven fabrics. Liquid permeable non-woven fabrics are especially suitable. Examples of the non-woven fabrics include ones made of fiber material such as synthetic fibers of olefins, e.g., polyethylene and polypropylene, polyesters, and polyamides; recycled fibers of rayon and cupra; and natural fibers of cotton, which fabrics are produced by any suitable process such as spun lacing, spun bonding, thermal bonding, melt blowing, or needle punching.

The back sheet 30 is arranged under the absorber 50 and is a liquid-impermeable sheet to prevent body fluid from leaching out or leaking out of the absorptive article 1. The back sheet 30 in this embodiment constitutes the outermost layer of the absorptive article 1.

Examples of the liquid-impermeable sheet include polyethylene or polypropylene sheets having at least waterproof property, preferably sheets also having moisture permeability in order to suppress humidity. Examples of the suitable sheet material having both waterproof property and moisture permeability include microporous sheet materials produced by forming a sheet from an olefin resin such as polyethylene or polypropylene containing inorganic filler through melting and kneading and then uniaxially or biaxially stretching the sheet.

Alternatively, a laminated non-woven fabric composed of a liquid-impermeable film and an air-permeable nonwoven fabric layer may be used. The laminated nonwoven fabric is composed of, for example, a polyethylene sheet laminated with a nonwoven fabric, having both liquid-impermeability and air permeability.

The back sheet 30 should have liquid-impermeability, but does not necessarily need to have moisture permeability.

The gather sheets 40 and 40 are disposed over the top sheet 20 at both side edges, respectively, of the absorber 50, along the longitudinal direction from the belly side portion 11 to the back side portion 12.

The outer portions of the gather sheets 40 and 40 with respect to the width direction (transverse direction) are fixed to the upper surfaces of the top sheet 20 and the back sheet 30 lateral to the absorber 50. The inner portions of the gather sheets 40 and 40 with respect to the width direction are not fixed to the top sheet 20 or the back sheet 30, and each has a three-dimensional-gather elastic member 401, such as a rubber thread, along the longitudinal direction (anteroposterior direction) to form a pair of standing three-dimensional gathers that can be stretchably deformed corresponding to a body shape of a wearer.

The absorber 50 extends from the belly side portion 11 through the crotch portion 13 to the back side portion 12.

Figure 3:
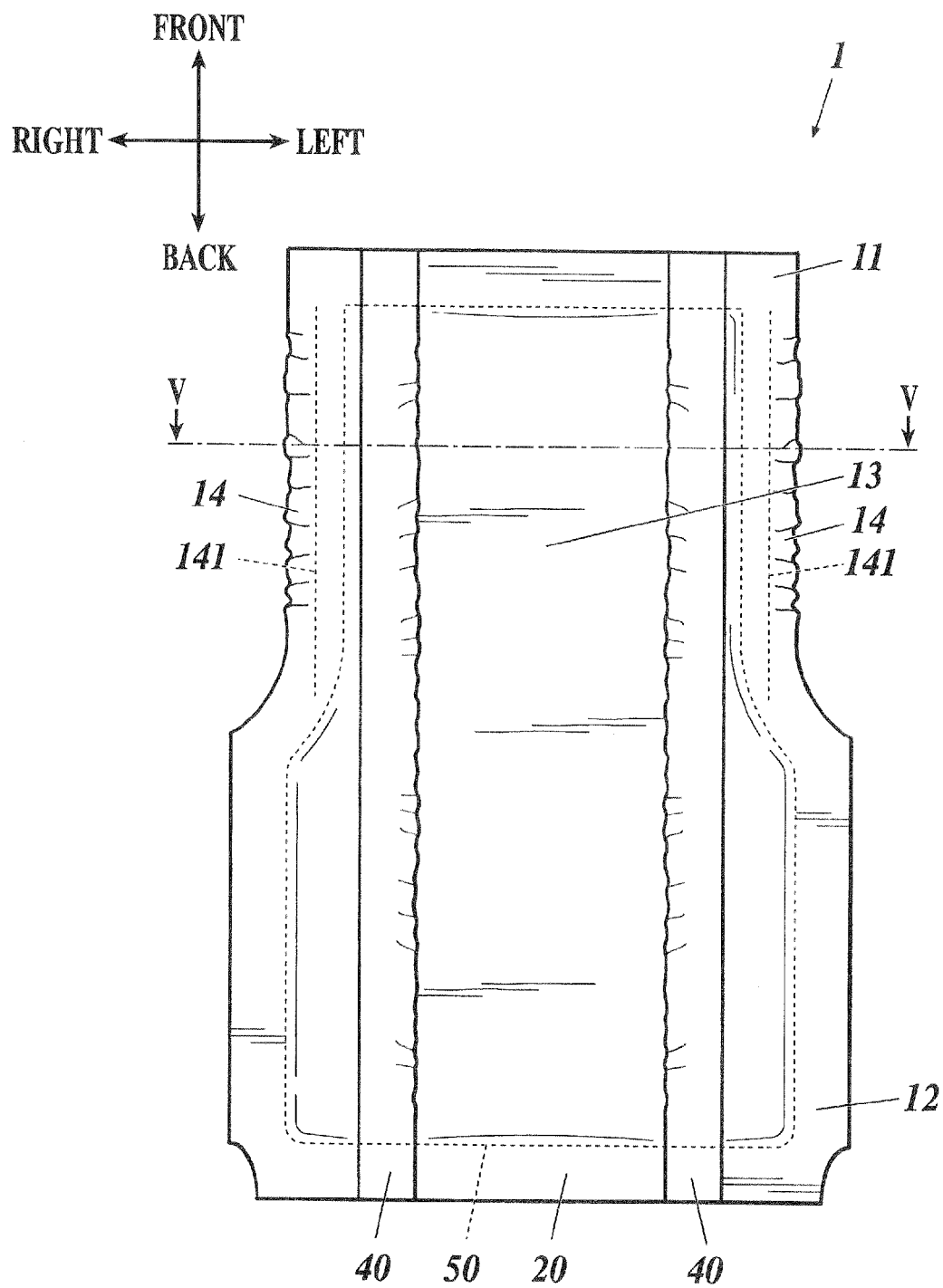
FIG. 3 is a planar development view illustrating an upper portion of an absorptive article of the present embodiment.
Figure 4:
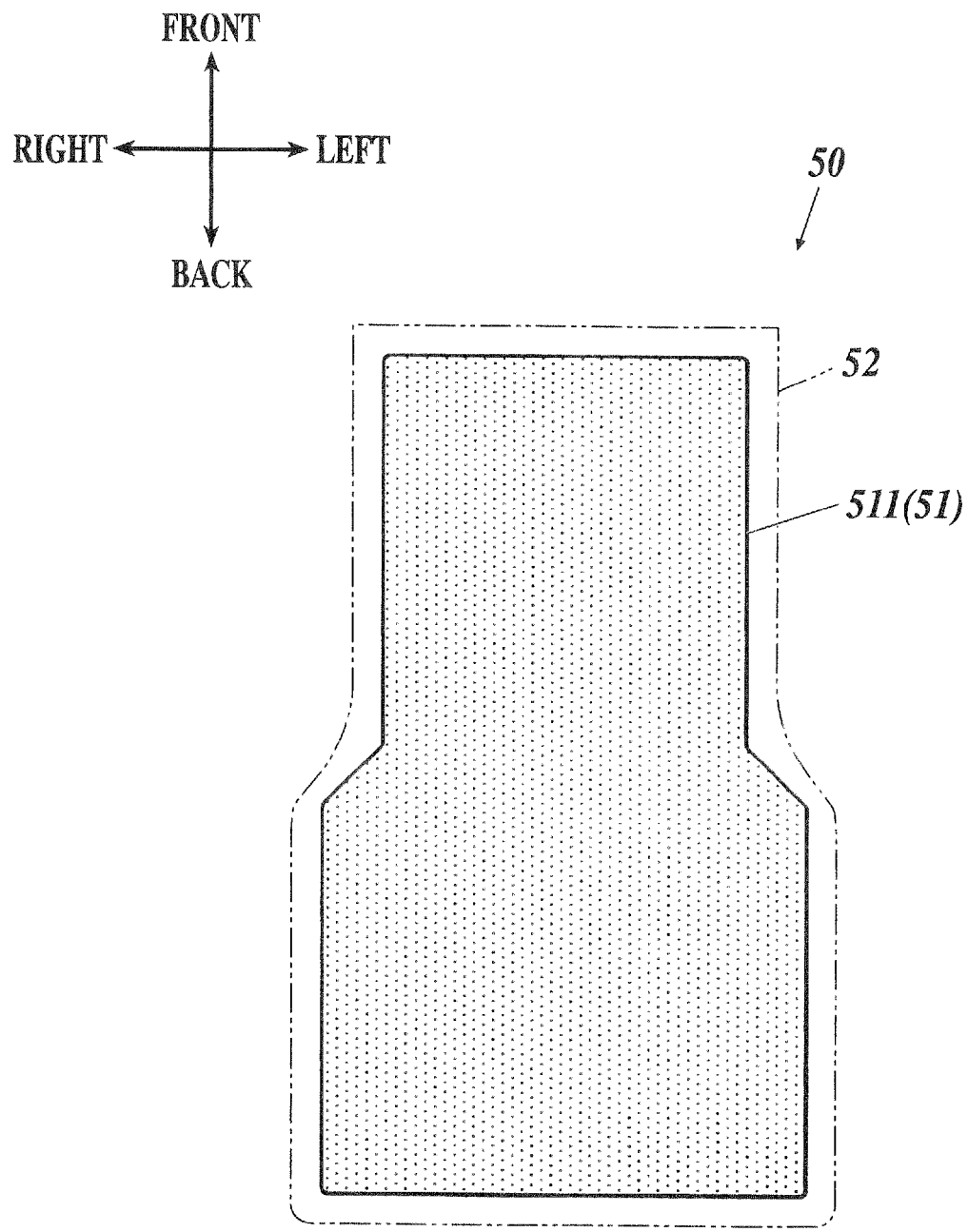
FIG. 4 is a planar development view illustrating an upper portion of an absorber of an absorptive article of the present embodiment.

The absorber 50, which plays a role in absorbing watery components such as urine as body fluid when the absorptive article 1 is used, has an absorbent core 51 covered with a liquid-permeable crepe paper 52. The outer shape of the absorber 50 is represented by dashed lines in FIGS. 1 to 3, and the outer shape of the crepe paper 52 covering the absorbent 50 is represented by a two-dot chain line in FIG. 4.

Figure 5:
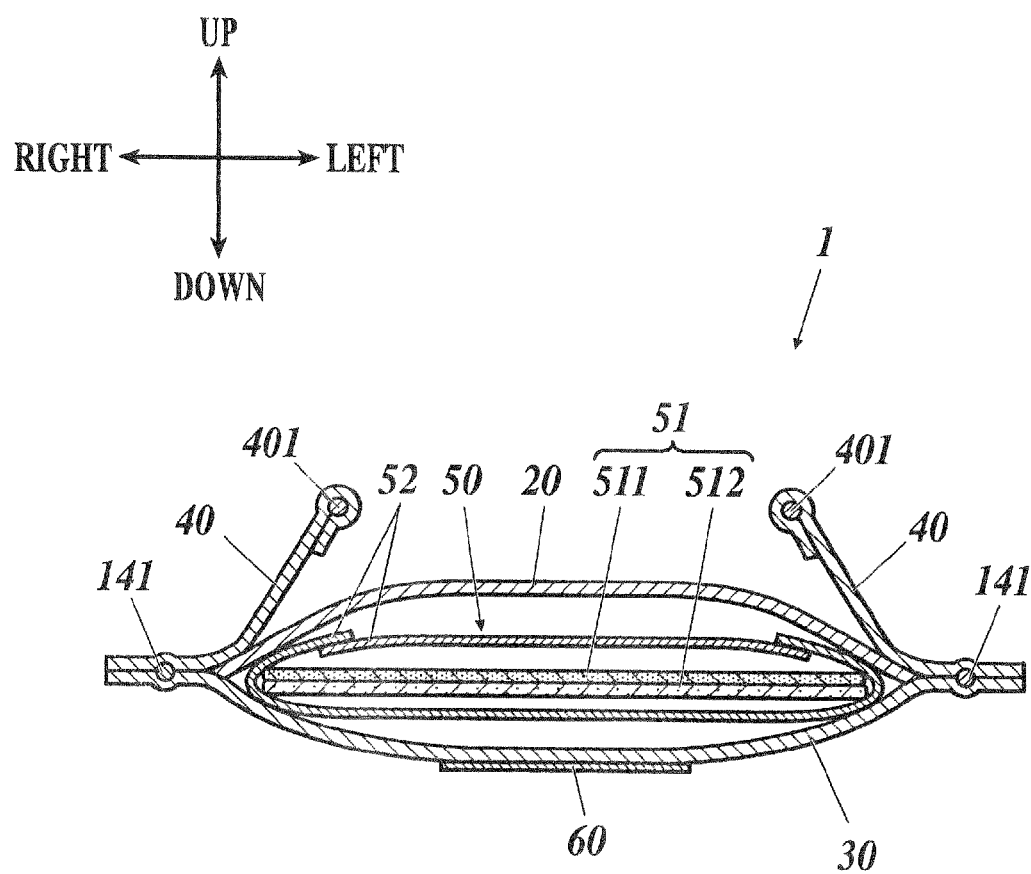
FIG. 5 is a cross-sectional view along the line V-V of FIG. 3.

The absorbent core 51 has a double-layer structure including an upper absorbent layer 511 disposed on the side of the top sheet 20 and a lower absorbent layer 512 disposed on the side of the back sheet 30 as illustrated in FIG. 5.

The upper absorbent layer 511 is elongated in the anteroposterior direction, and the back side portion 12 has a length in the transverse direction longer than those of the belly side portion 11 and the crotch portion 13.

The upper absorbent layer 511 is composed of a combination of pulp as absorbent material and a high water-absorption resin such as absorbent polymer.

The pulp used in the upper absorbent layer 511 is virgin pulp and the absorbent polymer used in the upper absorbent layer 511 is virgin polymer. Since the upper absorbent layer 511 is arranged close to the surface to be in contact with a human body (close to the top sheet 20), the upper absorbent layer 511 keeps a constant absorbing rate for the body fluid. The absorbing rate is appropriately adjusted depending on the ratio of the absorbent material such as pulp to the high water-absorption resin such as absorbent polymer, and depending on the type of the high water-absorption resin.

The lower absorbent layer 512 has a shape similar to that of the upper absorbent layer 511, and is arranged on the lower surface of the upper absorbent layer 511 (closer to the back sheet 30 among the layers of the absorbent core 51).

The lower absorbent layer 512 is also composed of a combination of pulp as absorbent material and a high water-absorption resin such as absorbent polymer.

The pulp used in the lower absorbent layer 512 contains recycled pulp. The recycled pulp is, for example, pulp recovered from rejected products during manufacturing processes, pulp recycled from used absorptive articles, or pulp composed of a combination thereof. The absorbent polymer used in the lower absorbent layer 512 contains recycled polymer. The recycled polymer is, for example, a polymer recovered from rejected products during manufacturing processes.

The recycled pulp and polymer can be recovered from rejected products, for example, disposable diapers for babies, bladder control pads for babies, disposable diapers for nursing, bladder control pads for nursing, and sanitary napkins.

The recycled pulp from used absorptive articles can be recovered from, for example, used disposable diapers for babies, used bladder control pads for babies, used disposable diapers for nursing, used bladder control pads for nursing, and used sanitary napkins.

Specifically, the rejected absorptive articles are fractured to be used as the recycled pulp or polymer.

In order to recover pulp components from used absorptive articles, unwoven fabrics and waterproof sheets are removed after water components are separated from the absorbent polymer. The pulp components can be recovered by any known method.

Since such a lower absorbent layer 512 varies considerably in quality depending on the recycled pulp or polymer to be used compared to the upper absorbent layer 511, it is preferable that the recycled pulp and polymer be compounded with virgin pulp and virgin polymer, with the compounding ratio of the virgin pulp and virgin polymer being up to 75%. This reduces the variation in absorption rate, and allows the quality of the absorptive article 1 to be free from influence of increase or decrease in supply of the recycled pulp or polymer.

It is preferable that the body-fluid absorbing rate of the upper absorbent layer 511 be adjusted to be higher than that of the lower absorbent layer 512 in the absorptive article 1, so that the body fluid is swiftly absorbed in the upper absorbent layer 511 and retained in the lower absorbent layer 512. The body fluid is thereby swiftly detached from the skin to reduce discomfort of wearer and burden to the skin.

Although any known crepe paper 52 can be used, it is preferable that the crepe paper 52 have a weight not lower than 15 gsm, in order to effectively make commingled foreign materials inconspicuous, which commingled foreign materials include, for example, remaining rubber threads, unwoven fabrics, and polymer sheets, contained in recycled pulp in the lower absorbent layer 512.

Instead of the crepe paper 52, a liquid-permeable unwoven fabric or a porous sheet may be used for covering the absorbent core 51 in the absorber 50.

The fixing member 60 is composed of an adhesive tape to bond the absorptive articles 1 to the outer body, whose adhesive surface is exposed when release paper is peeled off.

Figure 2:
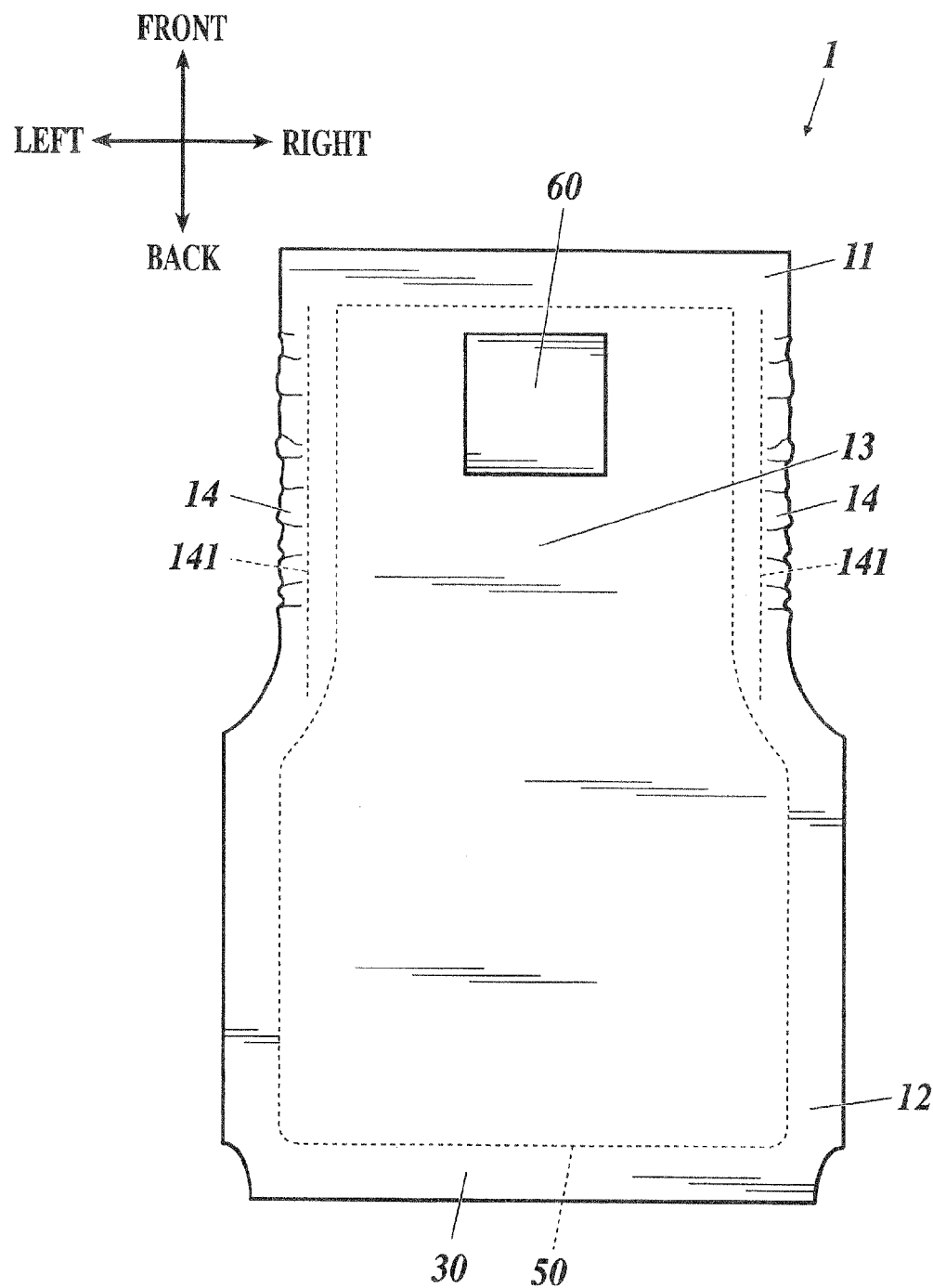
FIG. 2 is a planar development view illustrating a lower portion of an absorptive article of the present embodiment.

The fixing member 60, for example, has an approximately rectangular shape as illustrated in FIG. 2, and is arranged at the center of the belly side portion 11 on the surface opposite from a surface to be in contact with the wearer (the lower surface of the back sheet 30) when the absorptive article 1 is worn.

Preferably, the fixing member 60 is arranged at an anterior part of the belly side portion 11 in order to prevent the absorptive article 1 from being turned up or slipping. Since the adhesive tape has no moisture permeability (air permeability), it is preferable that the area of the fixing member 60 be less than 20% of the area of the back sheet 30 in order not to inhibit ventilation of the back sheet 30, especially in the case of employing a liquid-impermeable back sheet 30 having moisture permeability.

Any member capable of fixing the absorptive article 1 to the outer body, such as a face fastener, may be used as the fixing member 60 instead of an adhesive tape. However, it is preferable that the material be as soft as possible in order to easily follow the movement of the wear's body.

The absorptive article 1 of this embodiment described above includes a liquid-permeable top sheet 20, a liquid-impermeable back sheet 30, and an absorber 50 disposed between the top sheet 20 and the back sheet 30. The absorber 50 has a layered structure including an upper absorbent layer 511 disposed on the side of the top sheet 20 and a lower absorbent layer 512 disposed on the side of the back sheet 30. The upper absorbent layer 511 is composed of virgin pulp and virgin polymer, and the lower absorbent layer 512 contains recycled pulp and polymer recovered from rejected products during manufacturing processes.

That is, the recycled pulp and polymer are used only in the lower absorbent layer 512. Accordingly, foreign materials commingled with the recycled pulp and polymer are inconspicuous when viewed from the above, resulting in providing a satisfactory appearance of the absorptive article 1 regardless of the use of recycled pulp and polymers containing foreign materials.

In addition, although the recycled pulp, which has a fiber length shorter than that of virgin pulp, might reduce the absorption rate, the absorption rate is less affected by the fiber length because the recycled pulp is used only in the lower absorbent layer 512.

Further, although the recycled polymers tend to cause a variation in quality due to commingled polymers having various characteristics, such as high or low liquid permeability, the absorptive article 1 is less subject to adverse effect of the low-permeable polymer because the recycled pulp is used only in the lower absorbent layer 512. The adverse effect of the low-permeable polymer includes gel blocking on the absorber surface resulting in decrease in absorbing rate or increase in backward flow of the fluid.

The recycled pulp and polymer are suitably used as described above, in an ecological manner.

The absorptive article 1 of this embodiment described above has a lower absorbent layer 512 that contains virgin pulp and virgin polymer.

Consequently, the absorption rate is kept at constant, and quality of the absorptive article 1 is not affected by increase or decrease in supply of the recycled pulp or polymer.

Variation 1

Figure 6:
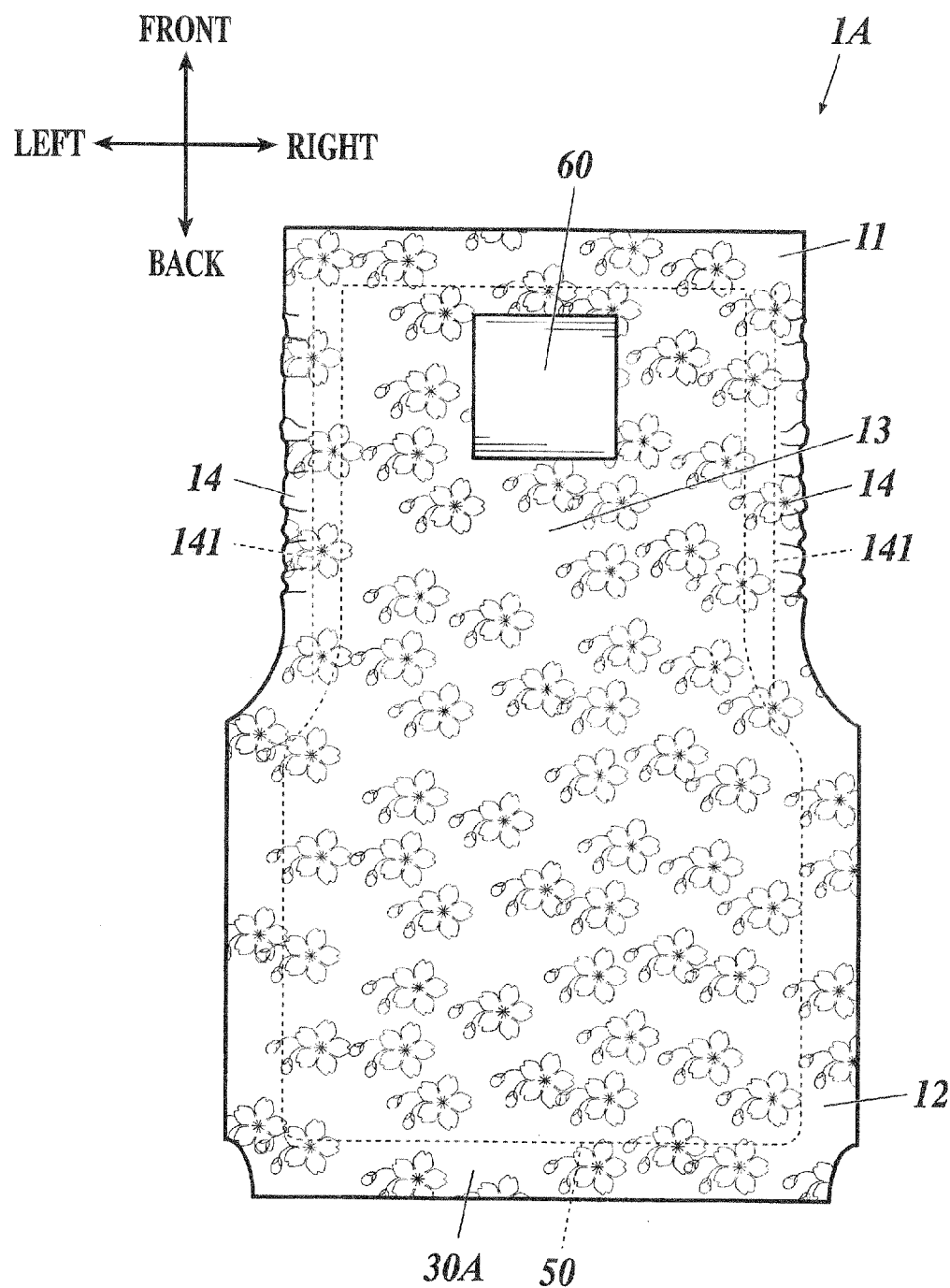
FIG. 6 is a plan view illustrating an absorptive article in Variation 1.

The back sheet 30 in the embodiment may have a predetermined color or pattern, as in a back sheet 30A of an absorptive article 1A illustrated in FIG. 6.

Specifically, foreign materials contained in the recycled pulp is effectively made inconspicuous by a deep color such as blue, green, or orange, or a pale color at high printing density.

Alternatively, the foreign materials contained in the recycled pulp can be camouflaged by predetermined drawing patterns or characters, especially by designs having colors such as pink, blue, green, orange, purple, and gray which are commonly used in rubber threads and polymer sheets of rejected products.

In Variation 1, the back sheet 30 having a color other than white can effectively make foreign materials inconspicuous when the foreign materials are commingled with the recycled pulp and polymers contained in the lower absorbent layer 512 of the absorber 50.

Variation 2

Figure 7:
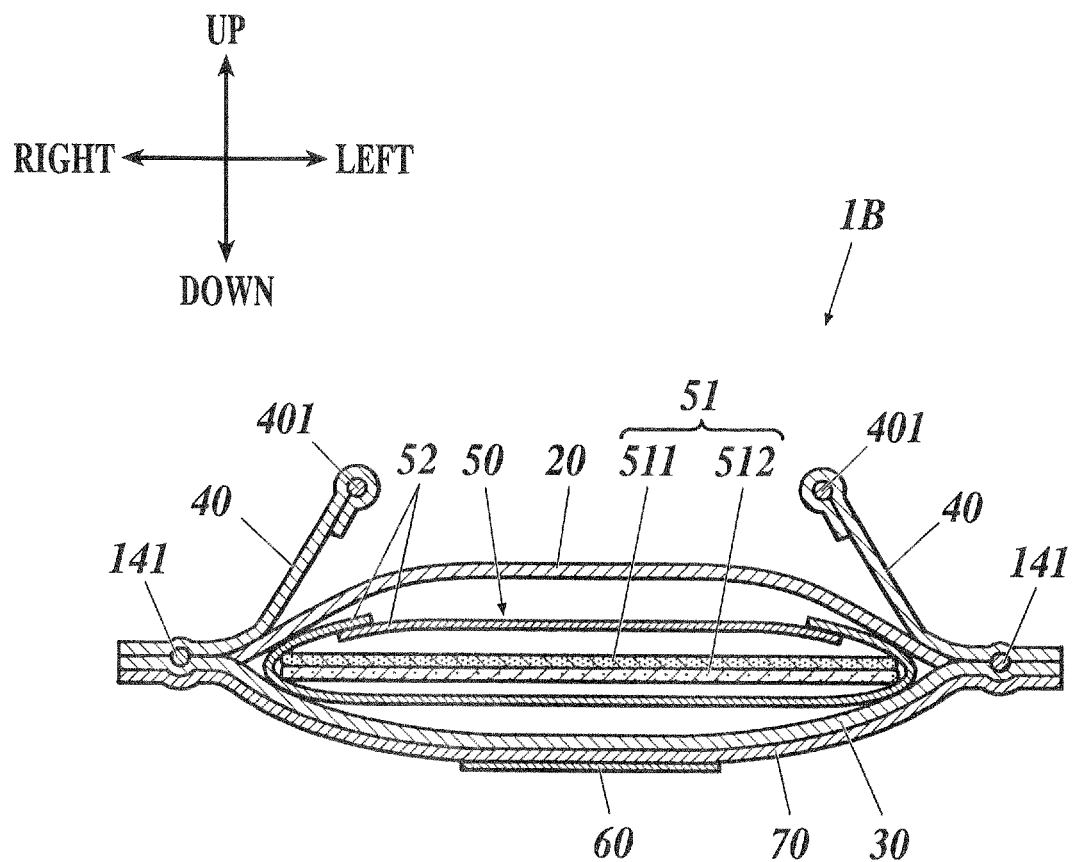
FIG. 7 is a cross-sectional view illustrating an absorptive article in Variation 2.

The back sheet 30 in this embodiment may have a second back sheet 70 that covers the lower surface of the back sheet 30 as in an absorptive article 1B illustrated in FIG. 7.

Specifically, the second back sheet 70 constitutes the back sheet, which is on the opposite side of the surface to be in contact with a wearer who wears the absorptive article 1B. The second back sheet 70 is composed of a non-woven fabric that covers a surface (lower surface) of the back sheet 30. The lower surface of the back sheet 30 is a surface opposite to the other surface of the back sheet 30 on the side of the top sheet 20.

Examples of the second back sheet 70 include, but are not limited to, chemical bond non-woven fabrics, thermal bond non-woven fabrics, spun lace non-woven fabrics, spunbond non-woven fabrics, melt-blown non-woven fabrics, heat-rolled non-woven fabrics, air through non-woven fabrics, liquid-impermeable non-woven fabrics, and sheets of a combination thereof. Alternatively, the sheet may be a liquid-impermeable sheet of, for example, polyethylene or polypropylene, having at least waterproof property.

In Variation 2, the second back sheet 70 can effectively make foreign materials inconspicuous when the foreign materials are commingled with the recycled pulp and polymers contained in the lower absorbent layer 512 of the absorber 50. Although not illustrated, the second back sheet 70 may have a predetermined color or pattern as illustrated in Variation 1.

Variation 3

Figure 8:
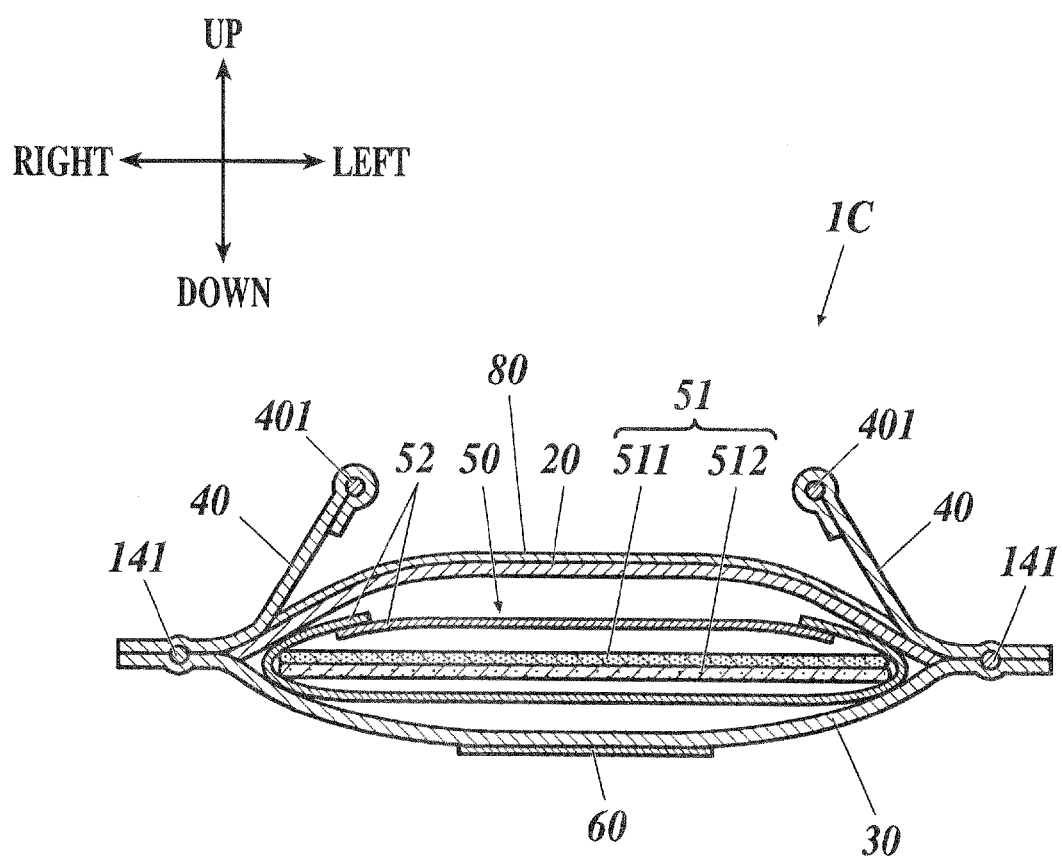
FIG. 8 is a cross-sectional view illustrating an absorptive article in Variation 3.

In the embodiments described above, the top sheet 20 may have a liquid-permeable second sheet 80 that covers the upper surface of the top sheet 20 as in the absorptive article 1C illustrated in FIG. 8.

Specifically, the second sheet 80 constitutes a surface to be in contact with a wearer who wears the absorptive article 1. The second sheet 80 is arranged to cover a surface (upper surface) of the top sheet 20. The upper surface of the top sheet 20 is a surface opposite to the other surface of the top sheet 20 on the side of the back sheet 30.

Examples of the liquid-permeable sheet include plain-woven nets from nylon or polyethylene terephthalate yarn, films or sheets having a large number of through holes, polyethylene or polypropylene sheets, and liquid-permeable woven or non-woven fabrics. Liquid permeable non-woven fabrics are especially suitable.

In Variation 3, the second sheet 80 provides satisfactory appearance as viewed from a surface to come into contact with a human body and prevents backward flow of the body fluid.

Although not illustrated, the top sheet 20 may have a second sheet 80, and the back sheet 30 may have a second back sheet 70 as illustrated in Variation 2.

In addition, the second back sheet 70 may have a predetermined color or pattern as illustrated in Variation 1.

Variation 4

Figure 9:
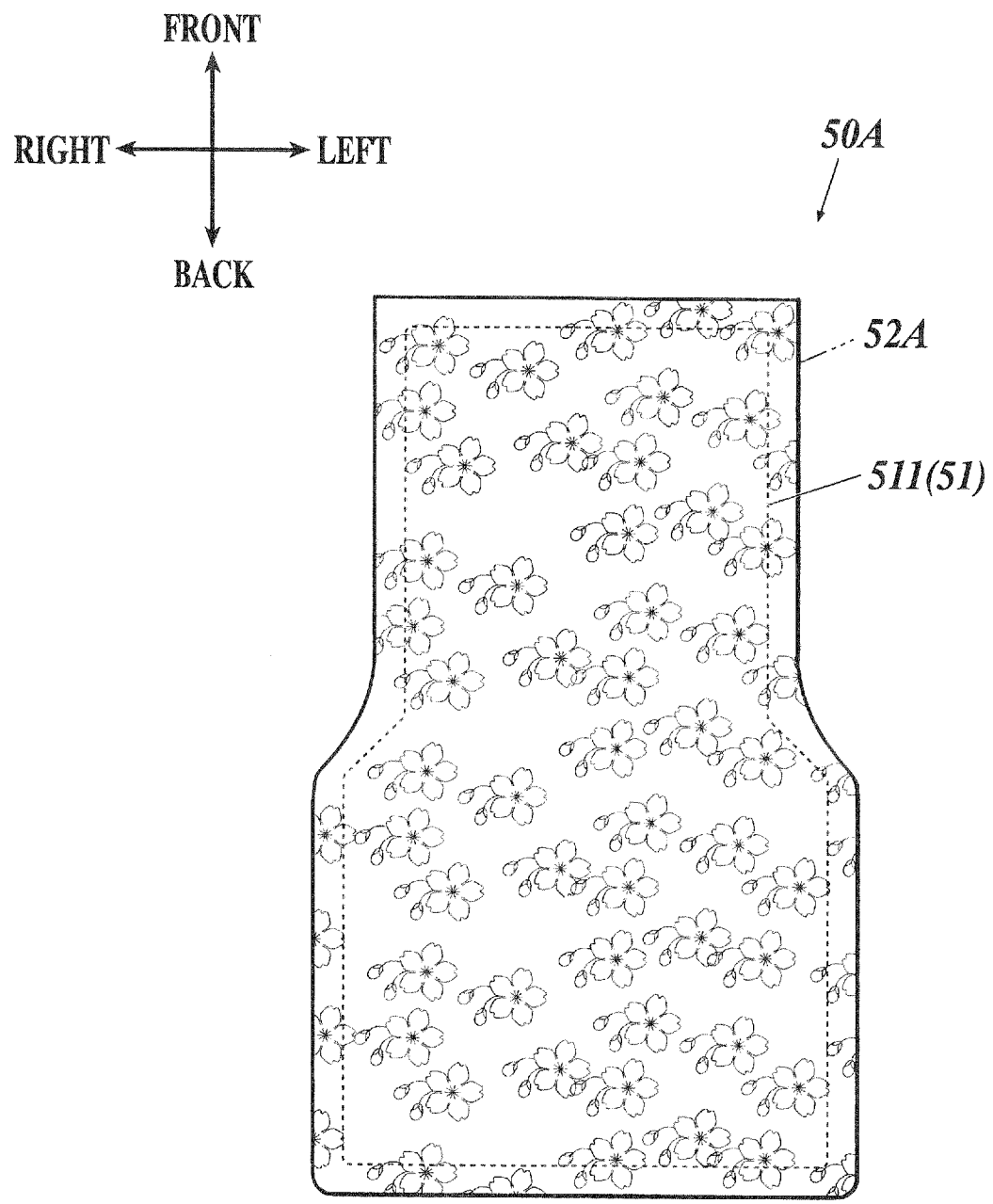
FIG. 9 is a plan view illustrating an absorber in Variation 4.

In the embodiments described above, the absorber 50 may be covered with a crepe paper 52A having a predetermined color or pattern as in an absorber 50A illustrated in FIG. 9.

Although any colors or patterns can be applied to the crepe paper 52A, for example, the colors or patterns described in Variation 1 can be suitably used.

In Variation 4, the color or pattern applied, to the crepe paper 52A effectively makes foreign materials inconspicuous when the foreign materials are commingled with the recycled pulp and polymers contained in the lower absorbent layer 512 of the absorber 50.

Variation 5

Figure 10:
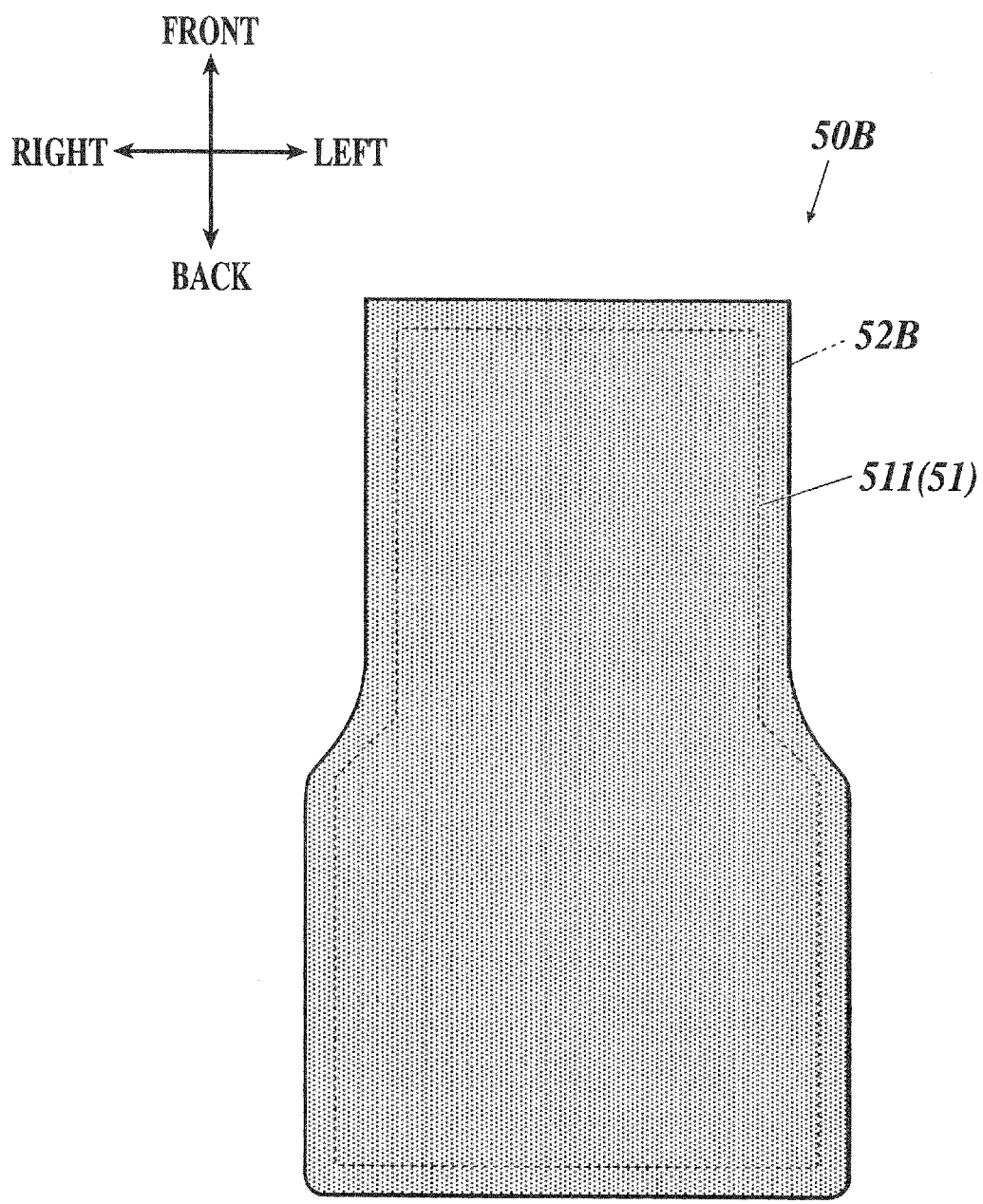
FIG. 10 is a plan view illustrating an absorber in Variation 5.

In the embodiments described above, the absorber 50 may be covered with a sheet 52B containing activated carbon as in an absorber 50B illustrated in FIG. 10.

In Variation 5, the sheet 52B containing activated carbon effectively makes foreign material inconspicuous because the sheet 52B is colored with activated carbon, and at the same time, the sheet 52B has odor eliminating and antibacterial effects.

The present invention is not limited to the embodiments described above and can be appropriately modified within the scope of the invention.

For example, although a bladder control pad is illustrated as the absorptive article in the embodiments and Variations 1 to 5, the absorptive article is not limited to this and can be applied to a disposable diaper for babies, a disposable diaper for nursing, a sanitary napkin, or the like.

The fixing member 60 may have any shape as long as the fixing member 60 is arranged at least in a belly side portion 11 of a surface (lower surface of the absorptive article 1), which surface is opposite to the surface to be in contact with a wearer. For example, the fixing member 60 may be elongated in the anteroposterior or transverse direction. Alternatively, the fixing member 60 may have a predetermined shape such as a T-shape.

The number of the fixing members 60 having the above-mentioned various shapes may be appropriately determined. For example, two fixing members may be arranged in the transverse or anteroposterior direction.

The absorptive article 1 may have flat gathers not only in the crotch portion 13 but also in a back side portion 12, for example. The flat gathers in the back side portion 12 makes the absorptive article 1 easily curve in the width direction, resulting in more effectively preventing leak of liquid.

In the embodiments, the absorptive article 1 may have only one of the flat gathers and the three-dimensional gathers.

The absorber core 51 is not limited to a double-layered structure as long as the absorber core 51 includes at least an upper absorbent layer 511 disposed on the side of the top sheet 20 and a lower absorbent layer 512 disposed on the side of the back sheet 30.

For example, an intermediate layer (not illustrated) having a predetermined function may be disposed between the upper absorbent layer 511 and the lower absorbent layer 512 to form a triple-layered structure.

INDUSTRIAL APPLICABILITY

The present invention can be used by manufacturers of absorptive articles.

REFERENCE NUMERALS 1, 1A, 1B, 1C: absorptive article
11: belly side portion
12: back side portion
13: crotch portion
14: leg periphery portion
141: flat-gather elastic member
20: top sheet
30 and 30A: back sheet
40: gather sheet
401: three-dimensional-gather elastic member
50, 50A, 50B: absorber
51: absorber core
511: upper absorbent layer
512: lower absorbent layer
52 and 52A: crepe paper
52B: sheet containing activated carbon
60: fixing member
70: second back sheet
80: second sheet

The invention claimed is:

1. An absorptive article comprising:
   a liquid-permeable top sheet;
   a liquid-impermeable back sheet; and
   an absorber disposed between the top sheet and the back sheet,
   wherein:
      the absorber has a layered structure comprising an upper absorbent layer disposed on a top-sheet side and a lower absorbent layer disposed on a back-sheet side;
      the upper absorbent layer comprises virgin pulp and virgin polymer; and
      the lower absorbent layer contains recycled pulp and recycled polymer.

2. The absorptive article according to claim 1, wherein the lower absorbent layer contains virgin pulp and virgin polymer.

3. The absorptive article according to claim 1, wherein the back sheet has a predetermined color or pattern.

4. The absorptive article according to a claim 1, further comprising a second back sheet that covers a surface of the back sheet, the surface being opposite to another surface of the back sheet on the top-sheet side.

5. The absorptive article according to claim 1, wherein the absorber is covered with crepe paper having a predetermined color or pattern.

6. The absorptive article according to claim 1, wherein the absorber is covered with a sheet containing activated carbon.

7. The absorptive article according to claim 1, further comprising a liquid-permeable second sheet that covers a surface of the top sheet, the surface being opposite to another surface of the top sheet on the back-sheet side.

* * * * *